United States Patent [19]

Okamoto et al.

[11] Patent Number: 5,420,319
[45] Date of Patent: * May 30, 1995

[54] CIS-OXALATO(TRANS-1-1,2-CYCLOHEXANEDIAMINE) PT(II) COMPLEX HAVING HIGH OPTICAL PURITY AND PROCESS OF PREPARING SAME

[75] Inventors: Koji Okamoto; Chihiro Nakanishi; Junichi Taniuchi; Junji Ohnishi; Yasunobu Komoda, all of Kanagawa, Japan

[73] Assignee: Tanaka Kikinzoku Kogyo K.K., Japan

[*] Notice: The portion of the term of this patent subsequent to Aug. 16, 2011 has been disclaimed.

[21] Appl. No.: 117,892

[22] Filed: Sep. 7, 1993

[30] Foreign Application Priority Data

May 21, 1993 [JP] Japan .................. 5-142824

[51] Int. Cl.⁶ .............................. G07F 15/00
[52] U.S. Cl. ...................................... 556/137
[58] Field of Search ............................ 556/137

[56] References Cited

U.S. PATENT DOCUMENTS

| | | | |
|---|---|---|---|
| 4,169,846 | 10/1979 | Kidani et al. | 260/429 R |
| 4,255,347 | 3/1981 | Kidani et al. | 260/429 R |
| 4,661,516 | 4/1987 | Brown et al. | 514/492 |
| 5,068,368 | 11/1991 | Nowatari et al. | 556/137 |
| 5,128,493 | 7/1992 | Nowatari et al. | 556/137 |

OTHER PUBLICATIONS

Chemical Abstracts, vol. 87, No. 1, issued Jul. 4, 1977, Kidani et al., "Synthesis and anti-tumor activities of platinum (II) complexes of 1,2-diaminocyclohexane isomers and their related isomers," p. 28, column 2, abs. No. 298z, J. Clin. Hematol. Oncol, 1977, 7(1), 197-209.

*Primary Examiner*—Paul J. Killos
*Assistant Examiner*—Porfirio Nazario-Gonzalez
*Attorney, Agent, or Firm*—Klauber & Jackson

[57] ABSTRACT

Disclosed is cis-oxalato(trans-1-1,2-cyclohexanediamine) Pt(II) complex having high optical purity and no toxicity and exhibiting anticancer performance, as shown in the below Formula.

Cis-oxalato(trans-1-1,2-cyclohexanediamine) Pt(II) complex of the invention possesses high optical purity or 99.94% or more e.e. and a melting point of 198.3° to 199.7° C. The complex is synthesized employing as starting material trans-1-1,2-cyclohexamediamine or a derivative of the trans-1-1,2-cyclohexanediamine optically resoluted by means of a high performance liquid chromatography.

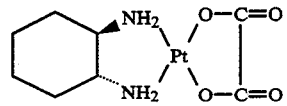

13 Claims, 3 Drawing Sheets

CIS-OXALATO(TRANS-1-1,2-CYCLOHEXANEDIAMINE) PT(II) COMPLEX HAVING HIGH OPTICAL PURITY AND PROCESS OF PREPARING SAME

BACKGROUND OF THE INVENTION

The present invention relates to cis-oxalato(trans-1-1,2-cyclohexanediamine) Pt(II) complex having high optical purity which may be employed as starting material of carcinostatic substance and a process of preparing same.

Trans-1-1,2-cyclohexanediamine can be obtained by reacting trans-dl-1,2-cyclohexanediamine with tartaric acid to form diastereomers and optically resoluting the respective diastereomers by means of a recrystallization method utilizing the difference of solubilities of the respective diastereomers. However, this method possesses a limitation because the solubility difference is not large so that it is reported that optical purity of 99.5 % or more cannot be industrially attained.

Accordingly, in order to obtain a platinum complex represented by Formula 1 having high optical purity, after the resolution of cis-trans stereoisomers of 1,2-cyclohexanediamine which is starting material for the preparation of the platinum complex in accordance with a resolution refining process

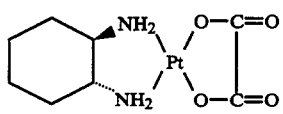

[Formula]

(Japanese patent publication No.61-4827), the optical resolution of the trans isomer is conducted by, in accordance with a normal process, forming a diastereomer by means of tartaric acid followed by its recrystallization. A platinum complex prepared by employing this resoluted isomer is further optically resoluted by means of high performance liquid chromatography (hereinafter referred to as "HPLC method") to produce the platinum complex (Formula 1) having the high optical purity (U.S. patent application Ser. No. 08/043,901 and European patent application No.93830160.3). The optical resolution of the final product is conventionally required because the resolution and refining of the trans-1-1,2-cyclohexanediamine is insufficient. Since the trans-1-1,2-cyclohexanadiamine is the important starting material of cis-oxalato(trans-1-1,2-cyclohexanadiamine) Pt(II) complex which is the starting material of a carcinostatic agent, the trans-1-1,2-cyclohexanediamine having stably higher optical purity has been required.

The platinum complex (Formula 1) has been synthesized in accordance with a preparation process shown as the below equation (Formula 2).

Many optically active pharmaceuticals may have a considerable difference in carcinostatic activities and their side effects due to their isomerism so

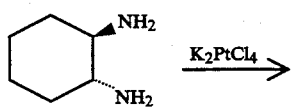

[Formula 2]

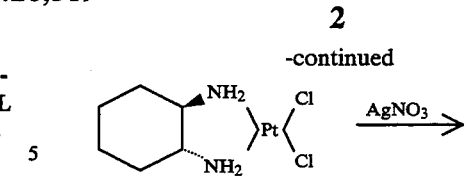

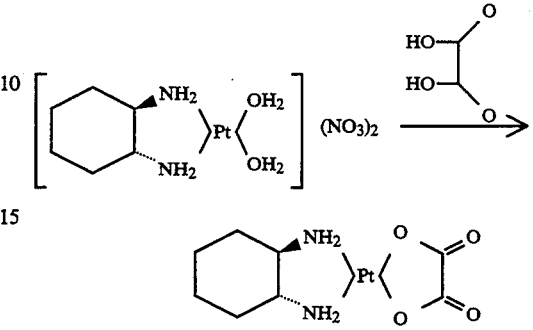

that their optical purity is important when they are utilized as the pharmaceuticals.

SUMMARY OF THE INVENTION

In these viewpoints, an object of the present invention is to provide cis-oxalato(trans-1-1,2-cyclohexanediamine) Pt(II) complex having high optical purity through complete optical resolution and its preparation process.

Another object of the invention is to provide the Pt(II) complex having the optical purity of 99.94 % or more and its preparation process.

Tile cis-oxalato(trans-1-1,2-cyclohexanediamine) Pt(II) complex having the high optical purity represented by Formula 1 of the invention can be obtained in accordance with one of the following processes.

Commercially available 1,2-cyclohexanediamine (for example, trans-1-1,2-cyclohexanediamine made by Aldrich, cis, trans-dl-mixed-1,2-cyclohexanediamine made by Tokyo Kasei K.K., and trans-1-1, 2-cyclohexanediamine made by Wako Junyaku K.K.) is employed. After the cyclohexanediamine made by Tokyo Kasei is resoluted into its cis and trans-stereoisomers in accordance with the above resolution refining process, trans-1-1,2-cyclohexanediamine having the high optical purity can be obtained employing the trans-isomer through one of the below three processes of optical resolution.

① The trans-1-1,2-cyclohexanediamine is reacted with L-(+)-tartaric acid to form a diastereomer. A filler prepared by, for example, chemically bonding (1R,2S)-2-carboxymethylamino-1,2-diphenylethanol to silica gel to which a metal ion (Cu$^{2+}$) is coordinated is packed in a column having, for example, an inner diameter of 4.6 mm and a height of 25 cm which is then employed as a resolution column. The resolution may be carried out by employing the column through which the diastereomer passes in accordance with the HPLC method. The mobile phase may be water and the detection may be performed by employing a polarimeter detecting 589 nm as a detector. An alkaline solution is added to the aqueous solution eluted to obtain the trans-1-1,2-cyclohexanediamine completely resoluted.

② The trans-1-1,2-cyclohexanediamine is reacted with a benzoyl derivative, preferably orthophthalaldehyde, to form a diastereomer. As a resolution column, ULTRON ES-OVM having an inner diameter of 4.6 mm and a height of 15 cm made by Shinwa Kako K.K. is, for example, employed. The resolution may be carried out by employing the column through which the diastereomer passes in accordance with the HPLC method. The mobile phase may be 20 nM of potassium dihydrogen phosphate (pH 5.6) and ethanol in a volume ratio of 100:7, and the detection may be performed by employing ultraviolet ray at 220 nm. Then, 1-N hydrochloric acid is added to the aqueous solution eluted to obtain the trans-1-1, 2-cyclohexanediamnie completely resoluted.

③ The trans-1-1,2-cyclohexanediamnie is dissolved in water. A filler prepared by, for example, chemically bonding L-proline to silica gel to which a metal ion (Cu$^{2+}$) is coordinated is packed in a column which is then employed as a resolution column. The resolution may be carried out by employing the column through which the diastereomer passes in accordance with the HPLC method. The mobile phase may be water and the detection may be performed by employing a polarimeter detecting 589 nm as detector. The water is removed from the aqueous solution eluted to obtain the trans-1-1,2-cyclohexanediamnie completely resoluted.

All the cis-oxalato(trans-1-1,2-cyclohexanediamine) Pt(II) represented as Formula 1 obtained by employing the trans-1-1,2-cyclohexanediamine having the high optical purity obtained in the above respective procedures ①, ② and ③ possesses high optical purity so that the optical resolution thereafter described in U.S. patent application Ser. No. 08/043,901 or European patent application No. 93830160.3 can be omitted. The preparation process of the cis-oxalato(trans-1-1,2-cyclohexanediamine) Pt(II) described therein is as follows.

Trans-1-1,2-cyclohexanediamine and equimolar potassium tetrachloroplatinate [K$_2$PtCl$_4$] are dissolved in water and reacted for over 10 hours at room temperature to produce the crystal of the cis-dichloro(trans-1-1,2-cyclohexanediamine) Pt(II) represented as Formula 3.

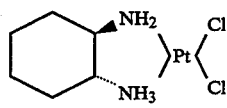

[Formula 3]

Then, water is added to the compound of Formula 3 for suspending to which is added a silver nitrate (2 mols) aqueous solution. The both are allowed to react in dark for over 24 hours and silver nitrate is removed by filtration to obtain an aqueous solution of cis-diaquo(trans-1-1,2-cyclohexanediamine) Pt(II) nitrate. After potassium iodide is added to this aqueous solution for removing the excess silver ion as silver iodide by mean of filtration and the aqueous solution is refined and decolorized with active carbon, equimolar oxalic acid in respect of the potassium tetrachloroplatinate is added to the aqueous solution to obtain the crude crystal of cis-oxalato(trans-1-1,2-cyclohexanediamine) Pt(II) after a two hour reaction. By recrystallizing this crude crystal from hot water, the cis-oxalato(trans-1-1,2-cyclohexanediamine) Pt(II) having high purity can be obtained.

The preparation process of this invention is as follows.

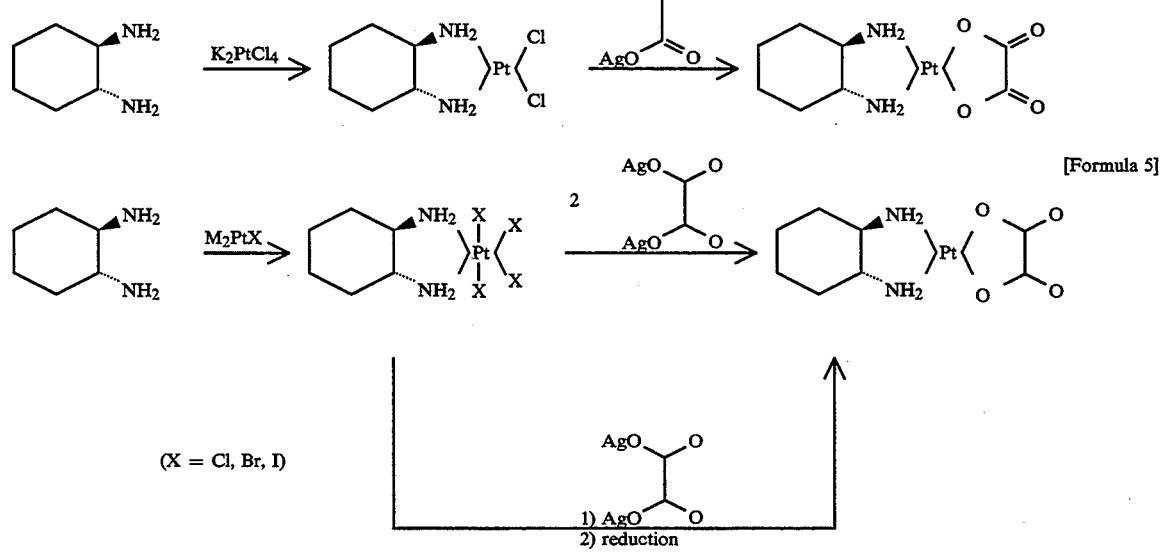

According to the present invention, cis-oxalato(trans-1-1,2-cyclohexanediamine) Pt(II) having high optical purity represented by Formula 1 is provided. Since this isomer contains no cis-oxalato(trans-d-1,2-cyclohexanediamine) Pt(II) which is an optical isomer, the former exhibits remarkably excellent results in connection with acute toxicity compared with that of the prior art and effective for providing pharmaceuticals having safety.

DETAILED DESCRIPTION OF THE INVENTION

Figure 1:
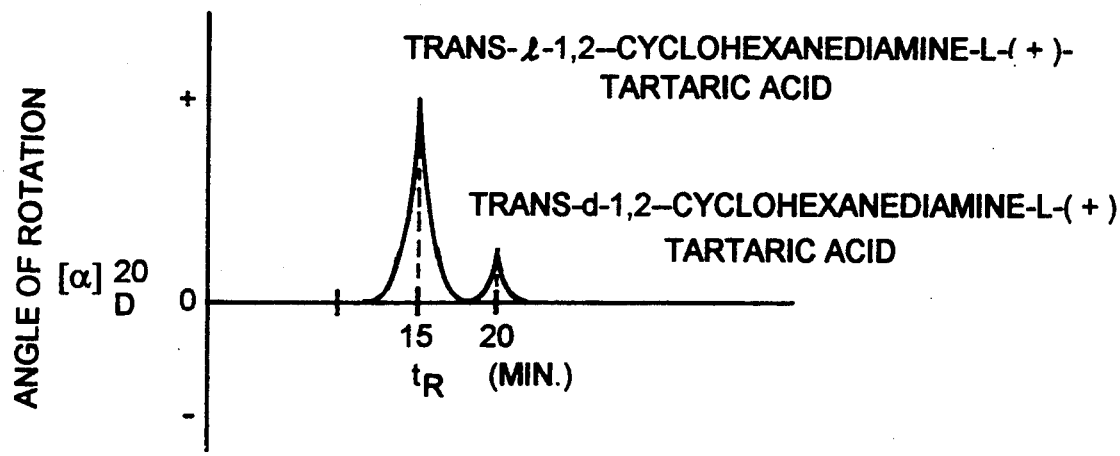
FIG. 1 is a chromatogram of isomers obtained by optical resolution of dl-1,2-cyclohexanediamine-L-(+)-tartaric acid by means of an HPLC method in Example 1 which shows a volume of elution at 589 nm of angle of rotation.

The preparation process of this invention will be described more in detail.

The cis-dichloro(trans-1-1,2-cyclohexanediamine) Pt(II) (Formula 3) obtained by reacting the trans-1-1,2-cyclohexanediamine obtained in the above procedures ①, ② and ③ with potassium tetrachloroplatinate [K$_2$PtCl$_4$] is suspended in water and equimolar silver oxalate is added thereto and reacted at a temperature of 0° to 100° C., preferably in a range of 20° to 60° C. for, generally, 0.5 to 4 hours. After silver chloride is removed by filtration and the filtrate is concentrated under a reduced pressure, a precipitated product is washed to obtain cis-oxalato(trans-1-1,2-cyclohexanediamine) Pt(II) represented by Formula 1.

The cis-tetrahalogeno(trans-1-1,2-cyclohexanediamine) Pt(IV) (Formula 6) obtained by reacting the trans-1-1,2-cyclohexanediamine obtained in the above procedures ①, ② and ③ with a platinum (IV) acid salt is suspended in water and two moles of silver oxalate is added thereto and reacted at a temperature range of 60° to 100° C. for, generally, 1 to 2 hours.

After silver halogenide is removed by filtration and the filtrate is concentrated under a reduced pressure, a precipitated product is washed to

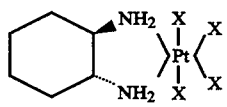

[Formula 6]

obtain the cis-oxalato(trans-1-1,2-cyclohexanediamine) Pt(II) represented by Formula 1.

After, on the other hand, the intermediate obtained above, the cis-tetrahalogeno(trans-1-1,2-cyclohexanediamine) Pt(IV) (Formula 6) is suspended in water and equimolar silver oxalate is added thereto for proceeding the reaction, it is reduced with a suitable reducing agent to also obtain the cis-oxalato(trans-1-1,2-cyclohexanediamine) Pt(II).

The cis-dihalogeno(trans-1-1,2-cyclohexanediamine) Pt(II) synthesized employing as starting material the trans-1-1,2-cyclohexanediamine obtained in the above procedures ①, ② and ③ having high optical purity is suspended in water and silver nitrate or silver sulfate is added thereto for proceeding the reaction. The resulting aqueous solution of the compound of Formula 7 is passed through a column packed with such anion exchange resin as Amberlite IRA-400, Dowex I and Diaion SA-1OA to obtain the compound of Formula 8. By reacting this with oxalic acid to obtain the cis-oxalato(-trans-1-1,2-cyclohexanediamine) Pt(II) represented by Formula 1.

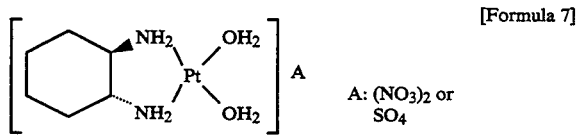

[Formula 7]

A: (NO$_3$)$_2$ or SO$_4$

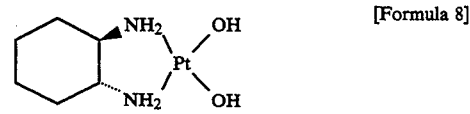

[Formula 8]

EXAMPLES

Then, a typical preparation process of the cis-oxalato(trans-1-1,2-cyclohexanediamine) Pt(II) of the present invention and its properties will be described in Examples, and Comparative Examples will be also presented which show that the compound is the mixture of optical isomers though it is well known. These Examples are not construed to limit the scope of the present invention.

EXAMPLE 1

Optical Resolution of Trans-dl-1,2-cyclohexanediamine-L-(+)-Tartaric Acid by Means of HPLC After 6.71 ml of water was added to 3.55 g of trans-dl-1,2-cyclohexanediamine to dissolve it under heating at 90° C. and then 2.21 g of L-(+)-tartaric acid and 1.34 ml of glacial acetic acid were gradually added and stirred, an aqueous solution of trans-dl-1,2-cyclohexanediamine-(+)-tartaric acid which was a diastereomer was obtained. The HPLC separation procedure was conducted under the following conditions employing the above solution.

Column: Filler prepared by chemically bonding (1R,2S)-2-carboxymethylamino-1,2-diphenylethanol to silica gel to which a metal ion (Cu$^{2+}$) was coordinated. Inner diameter: 4.6 mm Height: 25 cm Mobile phase: Water Column temperature: 40° C. Flow rate: 1.8 ml/min. Detector: Polarimeter 589 nm As shown in FIG. 1, the retention time (t$_R$) of trans-1-1,2-cyclohexanediamine-(+)-tartaric acid was 15 minutes and the retention time (t$_R$) of trans-d-1,2-cyclohexanediamine-(+)-tartaric acid was 20 minutes so that both were completely isolated. After sodium hydroxide was added to the respective diastereomers to make its pH alkaline, the diastereomers were extracted with ether and distilled under reduced pressure to produce as colorless liquid trans-1-1,2-cyclohexanediamine and trans-d-1,2-cyclohexanediamine.

EXAMPLE 2

Optical Resolution of Trans-dl-1,2-cyclohexanediamine-D-(−)-Benzol-Tartaric Acid by Means of HPLC An aqueous solution of trans-dl-1,2-cyclohexanediamine-D-(−)-bonzoyltartaric acid was obtained in accordance with the procedures of Example 1 except that D-(−)-benzoyltartaric acid and ethanol were employed in place of the L-(+)-tartaric acid and the water of Example 1, respectively. The HPLC separation procedure was conducted under the following conditions employing the above solution.

Figure 2:
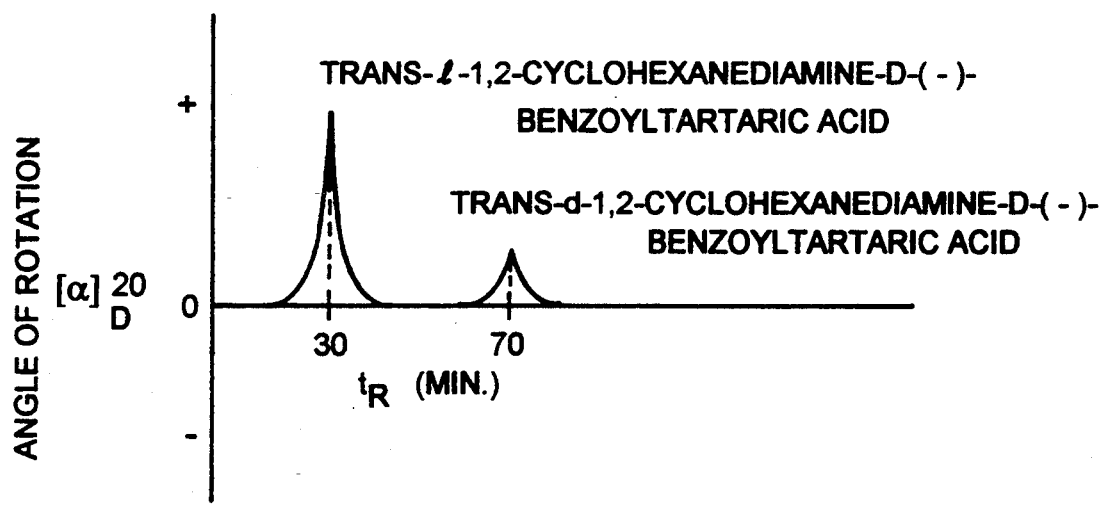
FIG. 2 is a chromatogram of isomers obtained by optical resolution of trans-dl-1,2-cyclohexanediamine- D-(−)-benzoyltartaric acid by means of an HPLC method in Example 2.

Column: Octadecylsilane Inner diameter: 4.6 mm Height: 25 cm Mobile phase: Water:Methanol=3:7 (volume ratio) Column temperature: 40° C. Flow rate: 1.0 ml/min. Detector: Polarimeter 589 nm As shown in FIG. 2, the retention time ($t_R$) of trans-1-1,2-cyclohexanediamine-D-(−)-benzoyltartaric acid was 30 minutes and the retention time ($t_R$) of trans-d-1,2-cyclohexanediamine-D-(−)-benzoyltartaric acid was 70 minutes so that both were completely isolated. After the isolation procedures the same as those of Example 1, trans-1-1,2-cyclohexanediamine and trans-d-1,2-cyclohexanediamine were obtained.

EXAMPLE 3

Optical Resolution of Trans-dl-1,2-cyclohexanediamine Orthophthal-Aldehyde Derivative by Means of HPLC After 11.4 mg of trans-dl-1,2-cyclohexanediamine was dissolved in 44 ml of phosphoric acid buffer (pH 7) and 20.1 g of orthophthalaldehyde was added thereto, the reaction was allowed to proceed at room temperature for a whole day and night to produce a solution of a trans-dl-1,2-cyclohexanediamine orthophthalaldehyde derivative. The HPLC separation procedure was conducted under the following conditions employing the above solution.

Figure 3:
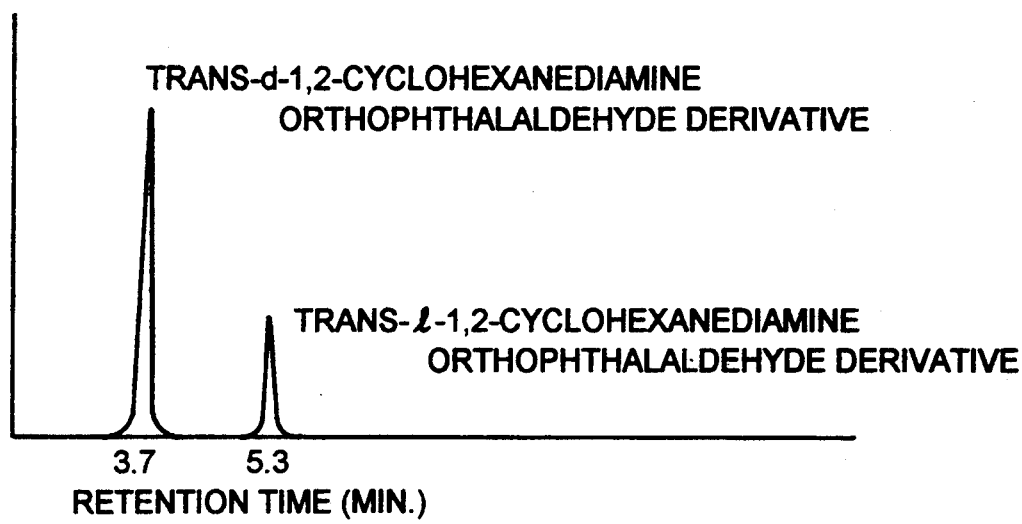
FIG. 3 is a chromatogram of isomers obtained by optical resolution of a trans-dl-1,2-cyclohexanediamine orthophthalaldehyde derivative by means of an HPLC method in Example 3 which shows a volume of elution as its relative absorption volume of ultraviolet ray of angle of rotation at 220 nm of angle of rotation.

Column: ULTRON ES-OVM made by Shinwa Kako K.K. (filler prepared by chemically bonding acidic glycoprotein to aminated silica gel) Inner diameter: 4.6 mm Height: 15 cm Mobile phase: 20 mM potassium dihydrogen phosphate (pH 5.6):ethanol=100:7 (volume ratio) Column temperature: 40° C. Flow rate: 2.0 ml/min. Detector: UV 220 nm As shown in FIG. 3, the retention time ($t_R$) of the trans-1-1,2-cyclohexanediamine orthophthalaldehyde derivative is 5.3 minutes and that of the trans-d-1,2-cyclohexanediamine orthophthalaldehyde was 3.7 minutes so that both were completely isolated. After 1-N hydrochloric acid was added to the respective derivatives and reacted at room temperature for 30 minutes, the derivatives were extracted with ether and distilled under reduced pressure to produce as colorless liquid trans-1-1,2-cyclohexanediamine and trans-d-1,2-cyclohexanediamine.

EXAMPLE 4

Optical Resolution of Trans-dl-1,2-cyclohexanediamine by Means of HPLC

In 100 ml of water was dissolved 1.00 g of trans-dl-1,2-cyclohexanediamine. The HPLC separation procedure was conducted under the following conditions employing the above solution.

Figure 4:
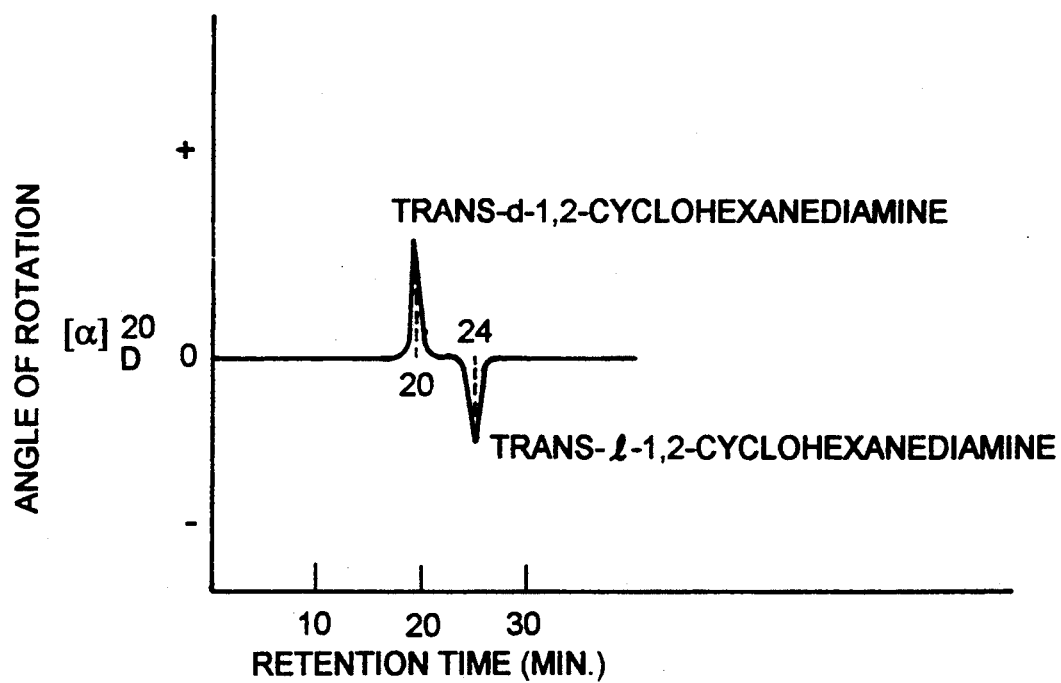
FIG. 4 is a chromatogram of isomers obtained by optical resolution of trans-dl-1,2-cyclohexanediamine by means of an HPLC method in Example 4.

Column: Filler prepared by chemically bonding L-prolin to silica gel to which a metal ion ($Cu^{2+}$) was coordinated. Inner diameter: 4.6 mm Height: 25 cm Mobile phase: Water Column temperature: 40° C. Flow rate: 1.8 ml/min. Detector: Polarimeter 589 nm As shown in FIG. 4, the retention time ($t_R$) of the trans-d-1,2-cyclohexanediamine was 20 minutes and that of the trans-1-1,2-cyclohexanediamine was 24 minutes so that both were completely isolated.

EXAMPLE 5

The HPLC separation procedure was conducted under the following conditions employing the solution of Example 4.

Figure 5:
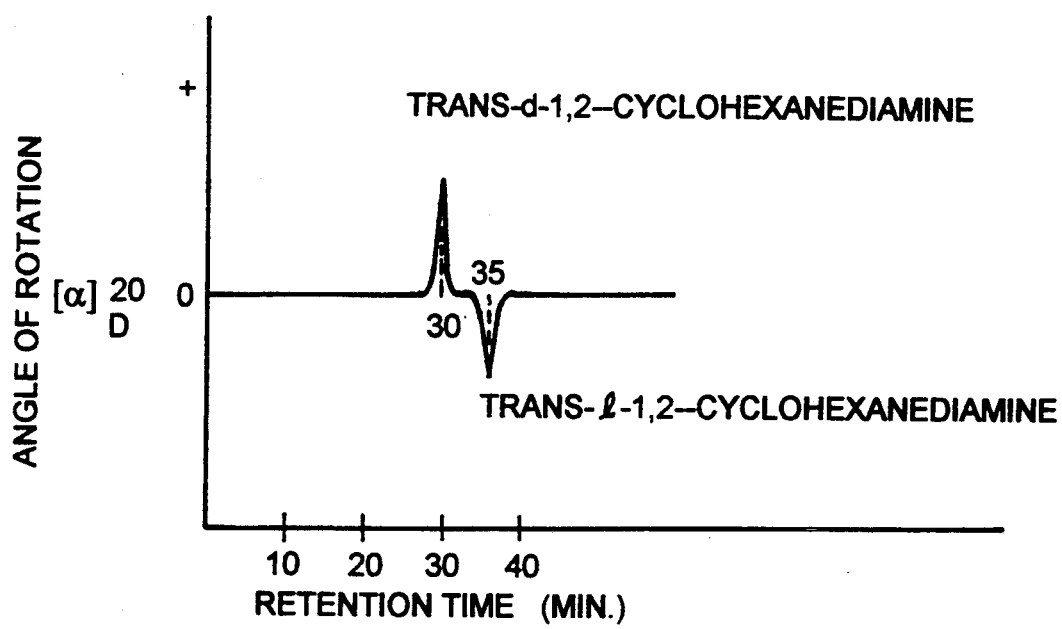
FIG. 5 is a chromatogram of isomers obtained by optical resolution of trans-dl-1,2-cyclohexanediamine by means of an HPLC method in Example 5.

Column: Filler prepared by adsorbing cellulose trisphenyl carbamate to silica gel Inner diameter: 4.6 mm Height: 25 cm Mobile phase: Ethanol:Methanol=50:50 (volume ratio) Column temperature: 40° C. Flow rate: 2.0 ml/min. Detector: Polarimeter 589 nm As shown in FIG. 5, the retention time ($t_R$) of the trans-d-1,2-cyclohexanediamine was 30 minutes and that of the trans-1-1,2-cyclohexanediamine was 35 minutes so that both were completely isolated.

Comparative Example 1

The diastereomer obtained in Example 1 was optically resoluted by means of recrystallization in place of the HPLC method. That is, when 67 ml of water was added to 35.5 g of trans-dl-1,2-cyclohexanediamine to dissolve it under heating at 90° C. and then 22.10 g of L-(+)-tartaric acid and 13.4 ml of glacial acetic acid were gradually added and stirred, an aqueous solution of trans-1-1,2-cyclohexanediamine-L-(+)-tartaric acid which was a diastereomer was obtained. After 9.23 g of this diastereomer was dissolved in a small amount of water, 5.64 g of sodium hydroxide was added, extracted with ether and distilled under reduced pressure to produce as colorless liquid 3.2 g of trans-1-1,2-cyclohexanediamine.

Comparative Example 2

The trans-1-1,2-cyclohexanediamine was obtained in accordance with the same procedures as those of Comparative Example 1 except that D-(−)-benzoyl tartaric acid and ethanol were employed in place of the L-(+)-tartaric acid and the water of Comparative Example 1, respectively.

EXAMPLE 6

Comparison of Optical Purity of Trans-1-1,2-cyclohexanediamine

The cis-oxalato(trans-1-1,2-cyclohexanediamine) Pt(II) was synthesized from the respective trans-1-1,2-cyclohexanediamine prepared in Examples 1, 2, 3, 4 and 5 and Comparative Examples 1 and 2 in accordance with a conventional method. The optical purity of the cis-oxalato(trans-1-1,2-cyclohexanediamine) Pt(II) after the below HPLC procedures was compared with an authentic sample.

Column: OC made by Daicel K.K. (filler prepared by adsorbing a cellulose carbamate derivative to silica gel) Inner diameter: 4.6 mm Height: 25 cm Mobile phase: Ethanol:Methanol=30:70 (volume ratio) Column temperature: 40° C. Flow rate: 2.0 ml/min. Detector: UV 254 nm The determination of the optical purity was conducted as follows. From an authentic sample, cis-oxalato(trans-1-1,2-cyclohexanediamine) Pt(II) (100% e.e.), a calibration curve was prepared. The mixed ratio of the optical isomer of the cis-oxalato(trans-1-1,2-cyclohexanediamine) Pt(II) obtained in Examples 1, 2, 3, 4 and 5 and Comparative Examples 1 and 2 was measured referring to the calibration curve and the optical purity was determined in accordance with the following equations.

Optical purity (%) = e.e. (%)
= [{cis-oxalato(trans-l-1,2-cyclohexanediamine) Pt(II) content}
− {cis-oxalato(trans-d-1,2-cyclohexanediamine) Pt(II) content}/
{cis-oxalato(trans-l-1,2-cyclohexanediamine) Pt(II) content}
+ {cis-oxalato(trans-d-1,2-cyclohexanediamine) Pt(II) content}] × 100
(e.e.: enantiomer excess)

Figure 6:
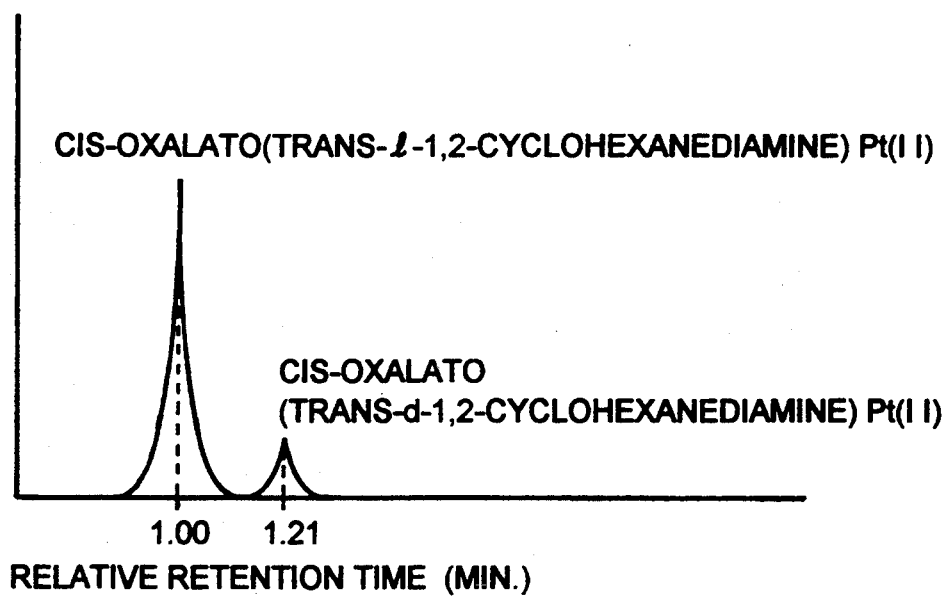
FIG. 6 is a chromatogram of isomers obtained by optical resolution of the mixture of cis-oxalato(trans-1-1,2-cyclohexanediamine) Pt(II) which is a standard sample and cis-oxalato(trans-d-1,2-cyclohexanediamine) Pt(II) which shows a volume of elution as its relative absorption volume of ultraviolet ray of angle of rotation at 254 nm of angle of rotation.

As shown in FIG. 6, while the relative retention time of the cis-oxalato (trans-l-1,2-cyclohexanediamine) Pt(II) was 1.00 minute, that of the cis-oxalato(trans-d-1,2-cyclohexanediamine) Pt(II) was 1.21 minutes. The relative standard deviation of the repeated HPLC injection precision was satisfactorily 0.04% or less.

The results of the determination of the optical purity are as shown in Table 1. The cis-oxalato(trans-l-1,2-cyclohexanediamine) Pt(II) synthesized from the trans-l-1,2-cyclohexanediamine optically resoluted by means of the HPLC method possesses higher optical purity than that of the cis-oxalato (trans-l-1,2-cyclohexanediamine) Pt(II) obtained through the recrystallization.

TABLE 1

|  |  | Optical Purity e.e. (%) |
|---|---|---|
| Example | 1 | 100.0 |
|  | 2 | 100.0 |
|  | 3 | 100.0 |
|  | 4 | 100.0 |
|  | 5 | 100.0 |
| Comparative Example | 1 | 99.0 |
|  |  | 99.0 |

EXAMPLE 7

① Preparation of cis-dichloro(trans-l-1,2-cyclohexanediamine) Pt(II)

After 46.8 g (0.41 mol) of the trans-l-1,2-cyclohexanediamine obtained in Examples 1 to 5 was reacted with 170 g (0.41 mol) of potassium tetrachloroplatinate in an aqueous solution at room temperature over 10 hours, 154.1 g (yield: 99%) of yellow needles of cis-dichloro(trans-l-1,2-cyclohexanediamine) Pt(II) were precipitated.

② Preparation of cis-oxalato(trans-l-1,2-cyclohexanediamine) Pt(II)

After 10.00 g (26.3 mmol) of the cis-dichloro(trans-l-1,2-cyclohexanediamine) Pt(II) obtained above was suspended in 800 ml of water, 7.99 g (26.3 mmol) of silver oxalate was added thereto and stirred for 2 hours at room temperature. After the precipitated silver chloride was removed, the obtained solution was concentrated to 100 ml. The deposited crystal was collected by filtration to obtain 8.3 g of crystals of cis-oxalato(trans-l-1,2-cyclohexanediamine) Pt(II) (yield: 80%). Optical purity: 100% e.e. Melting point: 198.3° to 199.7° C.

EXAMPLE 8

① Preparation of cis-tetrachloro(trans-l-1,2-cyclohexanediamine) Pt(IV)

After 45.7 g (0.40 mol) of the trans-l-1,2-cyclohexanediamine obtained in Examples 1 to 5 and 194.4 g (0.4 mol) of potassium hexachloroplatinate (IV) were dissolved in water and reacted for over 10 hours, 171.4 g (yield: 95%) of cis-tetrachloro(trans-l-1,2-cyclohexanediamine) Pt (IV) was obtained.

② Preparation of cis-oxalato(trans-l-1,2-cyclohexanediamine) Pt(II)

After 4.51 g (10.0 mmol) of the cis-tetrachloro(trans-l-1,2-cyclohexanediamine) Pt(IV) obtained ① of Example 8 was suspended in 800 ml of water, 6.08 g (20.0 mmol) of silver oxalate was added thereto and reacted for 1 hour under reflux. After insoluble substance was removed, the obtained solution was concentrated to 80 ml under reduced pressure, the deposited crystal was collected by filtration to obtain 3.18 g of cis-oxalato(-trans-l-1,2-cyclohexanediamine) Pt(II) (yield: 80%). Optical purity: 100% e.e. Melting point: 198.3° to 199.° C.

③ Preparation of cis-oxalato(trans-l-1,2-cyclohexanediamine) Pt(II)

After 4.51 g (10.0 mmol) of the cis-tetrachloro(trans-l-1,2-cyclohexanediamine) Pt(IV) obtained ① of Example 8 was suspended in 800 ml of water, 3.04 g (10.0 mmol) of silver oxalate was added thereto and reacted for 10 hours under reflux. After insoluble substance was removed, 3.40 g (20.0 mmol) of silver nitrate was added to the obtained solution. After, further, 250 mg (5 mmol) of hydrazine hydrate was added thereto and reacted for 3 hours at room temperature, 20 ml of an aqueous solution of 1-N sodium hydroxide was added and reacted for 1 hour. After insoluble substance was removed, the obtained solution was concentrated to 80 ml under reduced pressure, the deposited crystal was collected by filtration to obtain 1.59 g of cis-oxalato(-trans-l-1,2-cyclohexanediamine) Pt(II) (yield: 40%). Optical purity: 100% e.e. Melting point: 198.3° to 199.7° C.

EXAMPLE 9

① Preparation of cis-diaquo(trans-l-1,2-cyclohexanediamine) Pt(II)

After 4.00 g (10.5 mmol) of the cis-dichloro(trans-l-1,2-cyclohexanediamine) Pt(II) obtained in ① of Example 7 was suspended in 100 ml of distilled water, two moles of silver nitrate was added and reduced in dark for over 24 hours and silver chloride produced in the reaction was removed by filtration. After 0.12 g of potassium iodide was added to the filtrate and reacted for over 12 hours for precipitating excess silver ions as silver iodide, 10 mg of active carbon was added thereto for refining and decolorizing which was then removed by filtration.

② Preparation of cis-oxalato(trans-l-1,2-cyclohexanediamine) Pt(II)

A solution of a nitrate of cis-diaquo(trans-l-1,2-cyclohexane-diamine) Pt(II) thus obtained was passed through a column packed with 160 ml of Amberlite IRA-400 and eluted with distilled water. After 1.32 g (10.5 mmol) of oxalic acid dihydrate was added to this solution and reacted for 2 hours to obtain 3.33 g of cis-oxalato(trans-l-1,2-cyclohexanediamine) Pt(II) (yield: 80%) was obtained. Optical purity: 100% e.e. Melting point: 198.3° to 199.7° C.

What is claimed is:

1. Cis-oxalato(trans-l-1,2-cyclohexanediamine) Pt(II) complex having high optical purity represented by Formula 1 which possesses optical purity of 99.94% or more and a melting point between 198.3° C. and 199.7° C.

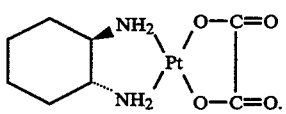
[Formula 1]

2. In a process for the preparation of cis-oxalato(-trans-1-1,2-cyclohexanediamine) Pt(II) complex of high optical purity and a melting point between 198.3° C. and 199.7° C., the improvement which comprises utilizing as the starting material for the synthesis of the complex trans-1-1,2-cyclohexanediamine or a derivative thereof which has been optically resoluted by high performance liquid chromatography, said complex being represented by the Formula:

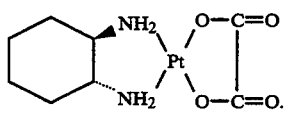

3. The process of claim 2 wherein the optically resoluted trans-1-1,2-cyclohexanediamine or derivative thereof is dissolved in water and reacted with a tetrahalogenoplatinum (IV) acid salt to produce cis-tetrahalogeno(trans-1-1,2-cyclohexanediamine) Pt(IV).

4. The process of claim 2 wherein the tetrahalogenoplatinum (IV) salt comprises potassium tetrachloroplatinate and the cis-tetratetrahalogeno(trans-1-1,2-cyclohexanediamine) Pt(IV) comprises cis-tetrachloro(-trans-1-1,2-cyclohexanediamine) Pt(IV).

5. The process of claim 4 wherein the cis-tetrachloro(trans-1-1,2-cyclohexanediamine) Pt(IV) is reacted with 2 moles of silver oxalate per mole of cis-tetrachloro(trans-1-1,2-cyclohexane-diamine) Pt(IV) to produce cis-oxalato(trans-1-1,2-cyclohexane-diamine) Pt(II) complex.

6. The process of claim 4 wherein the cis-tetrachloro(trans-1-1,2-cyclohexanediamine) Pt(IV) is reacted with equimolar silver oxalate and thereafter reduced with a suitable reducing agent to produce cis-oxalato(trans-1-1,2-cyclohexanediamine) Pt(II) complex.

7. The process of claim 2 wherein the optically resoluted trans-1-1,2-cyclohexanediamine or derivative thereof is dissolved in water and reacted with potassium tetrachloroplatinate to produce cis-dichloro(trans-1-1,2-cyclohexanediamine) Pt(IV).

8. The process of claim 7 wherein the cis-dichloro(-trans-1-1,2-cyclohexanediamine) Pt(IV) is suspended in water and reacted with equimolar silver oxalate to produce cis-oxalato(trans-1-1,2-cyclohexanediamine) Pt(II) complex.

9. The process of claim 7 wherein the cis-dichloro(-trans-1-1,2-cyclohexanediamine) Pt(IV) is suspended in water and reacted with silver nitrate or silver sulfate followed by elution with an anion exchange resin (OH form) to produce cis-dihydroxy(trans-1-1,2-cyclohexanediamine) Pt(IV) which is thereafter reacted with oxalic acid to produce cis-oxalato(trans-1-1,2-cyclohexanediamine) Pt(II) complex.

10. The process of claim 2 wherein the high performance liquid chromatography is carried out in a column packed with a filler comprised of a material selected from the group consisting of cellulose, a cellulose ester derivative, a cellulose carbamate derivative, an amylose carbamate derivative, a polymethacryl acid ester, β- and γ-cyclodextrin, a polymethacrylamide derivative, an acidic glycoprotein, L-proline, hydroxyproline, L-valine, a material prepared by adsorbing or binding (1R,2S)-2-carboxy-methylamino-1,2-diphenylethanol to silica gel, a material prepared by coordinating a metal ion to one of the aforesaid materials, a material prepared by adsorbing or binding a protein to aminated silica gel, a crown ether, a urea derivative chiral to silica gel treated with (3-aminopropyl)triethoxysilane, N(3,5-dinitrobenzoyl)-(R)-phenylglycine, a material chemically bonded to DNB-L-leucine and (S)-1-(α-naphthyl)-ethylamino-(S)-2-(4-chlorophenyl)isovaleric acid, an octadecylsilane and a silica gel.

11. The process of claim 2 wherein the optically resoluted trans-1-1,2-cyclohexanediamine derivative is prepared by reacting 1,2-cyclohexanediamine with a compound selected from the group consisting of L-(+)-tartaric acid, D-(−)-tartaric acid, L-(+)-benzoyltartaric acid and D-(−)-benzoyltartaric acid to form the diastereomer and optically resoluting the diastereomer by high performance liquid chromatography.

12. The process of claim 2 wherein derivative utilized as the optically resoluted trans-1-1,2-cyclohexane-diamine derivative is selected from the group consisting of an isoindolin derivative, a benzoyl derivative, an acetyl derivative, a 3,5-dinitrobenzoyl derivative and a para-nitrobenzoyl derivative.

13. The process of claim 2 wherein the high performance liquid chromatography is carried out by utilizing a column packed with a chiral filler and a polarimeter as a detector.

* * * * *